(12) United States Patent
Seitz et al.

(10) Patent No.: US 11,517,650 B2
(45) Date of Patent: Dec. 6, 2022

(54) ANTIBIOTIC IMPLANT COATINGS AND PROCESS FOR MANUFACTURING IMPLANT COATINGS

(71) Applicant: UNIVERSITY OF CINCINNATI, Cincinnati, OH (US)

(72) Inventors: Aaron Seitz, Cincinnati, OH (US); Michael Edwards, Cincinnati, OH (US); Erich Gulbins, Cincinnati, OH (US); Ryan Gobble, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 16/758,508

(22) PCT Filed: Oct. 24, 2018

(86) PCT No.: PCT/US2018/057282
§ 371 (c)(1),
(2) Date: Apr. 23, 2020

(87) PCT Pub. No.: WO2019/084117
PCT Pub. Date: May 2, 2019

(65) Prior Publication Data
US 2020/0254153 A1   Aug. 13, 2020

Related U.S. Application Data

(60) Provisional application No. 62/576,243, filed on Oct. 24, 2017.

(51) Int. Cl.
*A61K 31/16* (2006.01)
*A61L 31/16* (2006.01)
*A61L 27/54* (2006.01)

(52) U.S. Cl.
CPC .............. *A61L 31/16* (2013.01); *A61L 27/54* (2013.01); *A61L 2300/406* (2013.01); *A61L 2300/606* (2013.01); *A61L 2420/02* (2013.01)

(58) Field of Classification Search
CPC .... A61L 31/16; A61L 27/54; A61L 2300/406; A61L 2300/606; A61L 2420/02; A61L 2420/08; A61L 2400/18; A01N 25/34
See application file for complete search history.

(56) References Cited

U.S. PATENT DOCUMENTS

| 5,599,555 A | 2/1997 | El-Nokaly |
| 2003/0096097 A1 | 5/2003 | Vogt et al. |

(Continued)

FOREIGN PATENT DOCUMENTS

WO    2017100580 A1    6/2017

OTHER PUBLICATIONS

Extended European Search Report pertaining to corresponding European Patent Application No. 18870933.1 dated Jul. 13, 2021.

(Continued)

*Primary Examiner* — Carlos A Azpuru
(74) *Attorney, Agent, or Firm* — Dinsmore & Shohl LLP

(57) ABSTRACT

Methods for applying a coating to a surface of a substrate for inhibition and prevention of implant-associated complications (including implant-associated infections), methods for inhibiting and preventing implant-associated complications (including implant-associated infections), implant-associated infection inhibiting coatings, and coated devices are provided. Coating processes include a) providing a saturated or supersaturated solution of an antibiotic in a fast-evaporating or medium-evaporating organic solvent; b) coating the surface of the substrate with at least one application of solution, each application followed directly by a solvent evaporation period.

19 Claims, 12 Drawing Sheets

(56) References Cited

U.S. PATENT DOCUMENTS

2007/0134287 A1    6/2007  Troxel et al.
2010/0215716 A1    8/2010  Troxel et al.
2012/0270935 A1*  10/2012  Davis ..................... A01N 55/02
                                                           514/468
2013/0004651 A1*   1/2013  Fu-Giles .............. A61K 31/496
                                                           427/2.26

OTHER PUBLICATIONS

International Search Report & Written Opinion to corresponding PCT Application No. PCT/US2018/057282 dated Dec. 27, 2018.

\* cited by examiner

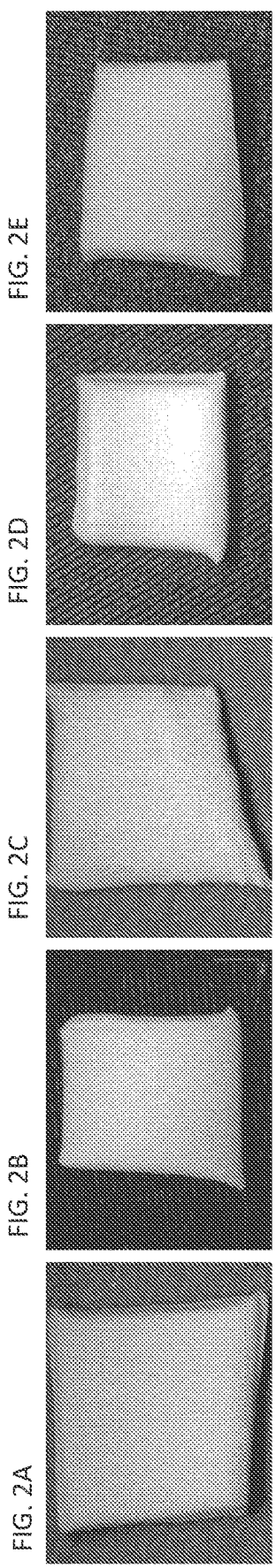
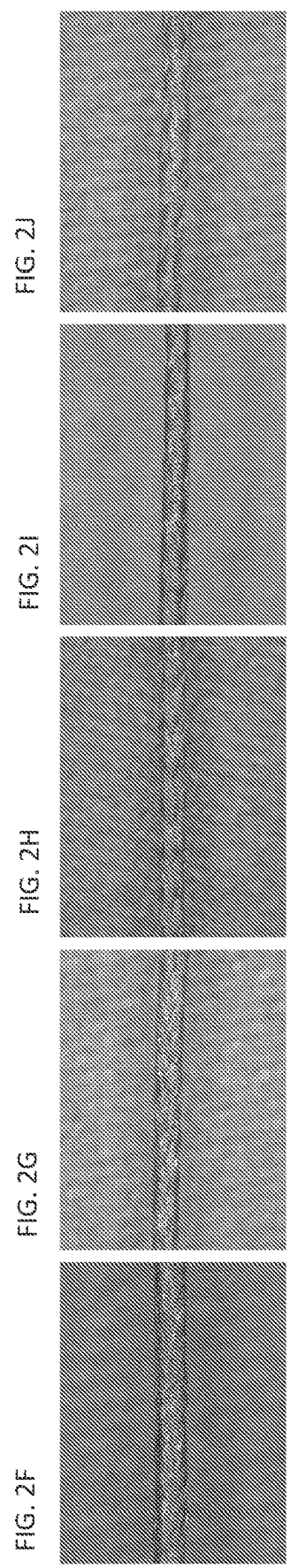
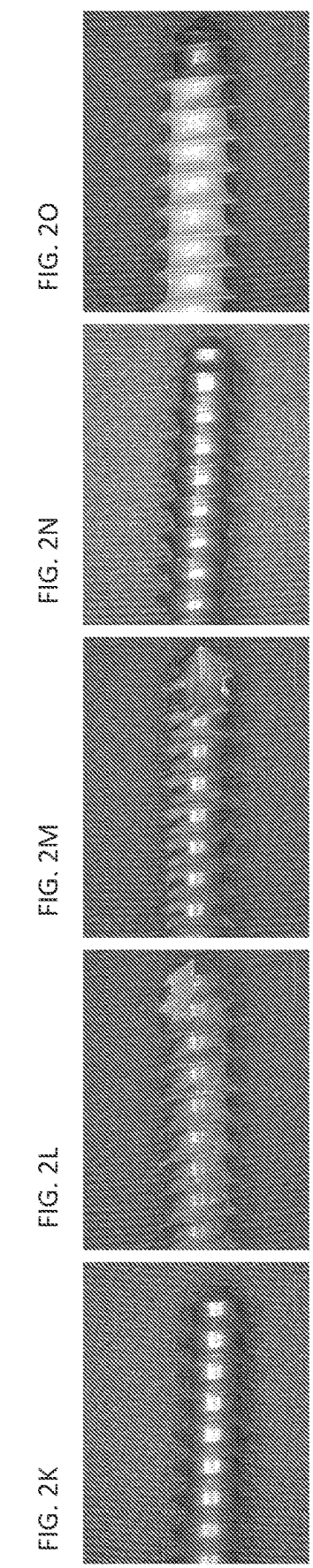

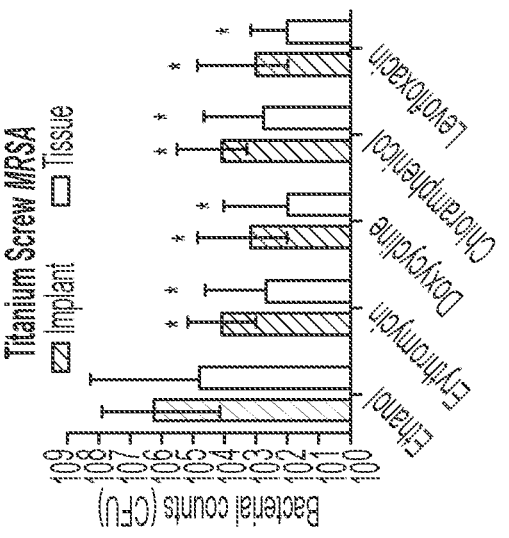
FIG. 5A
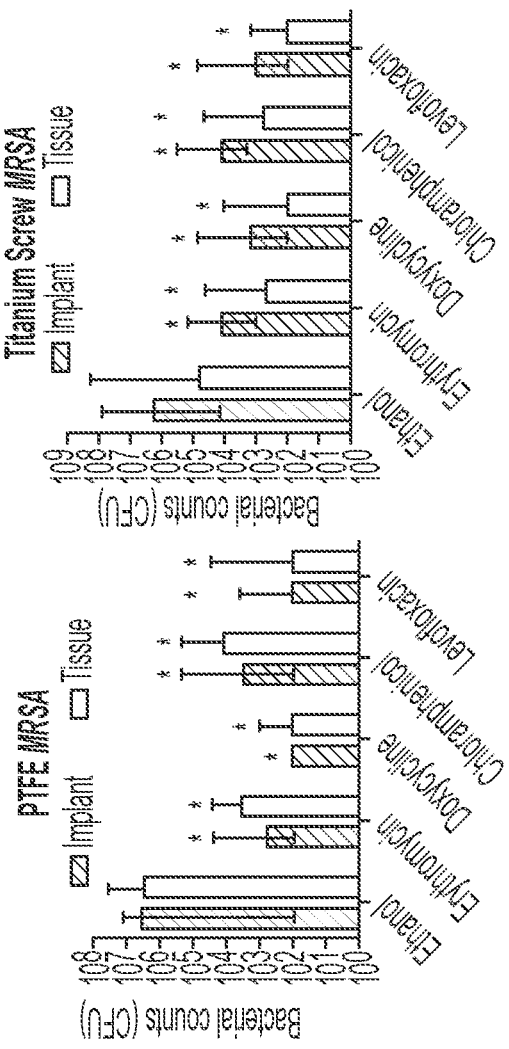
FIG. 5B
FIG. 5C
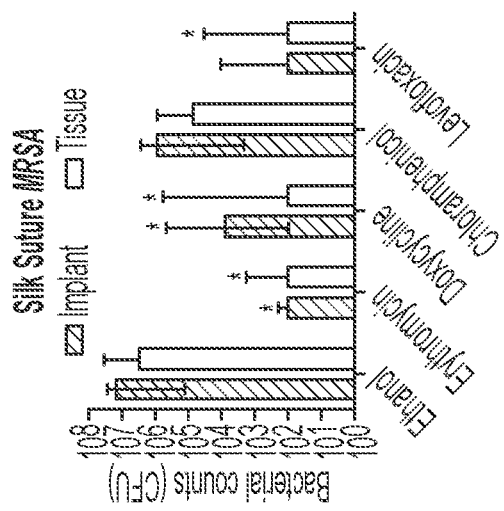
FIG. 5D
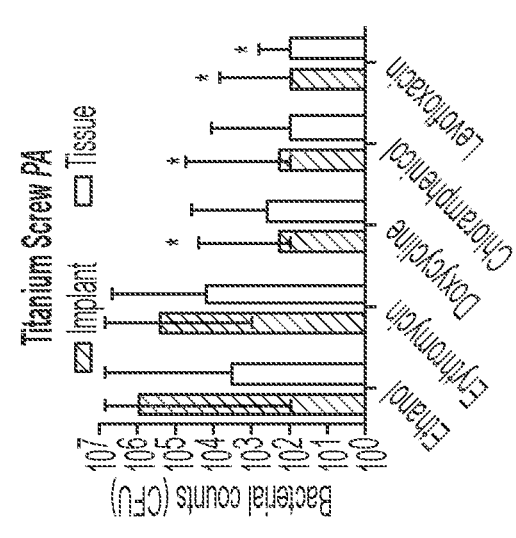
FIG. 5E
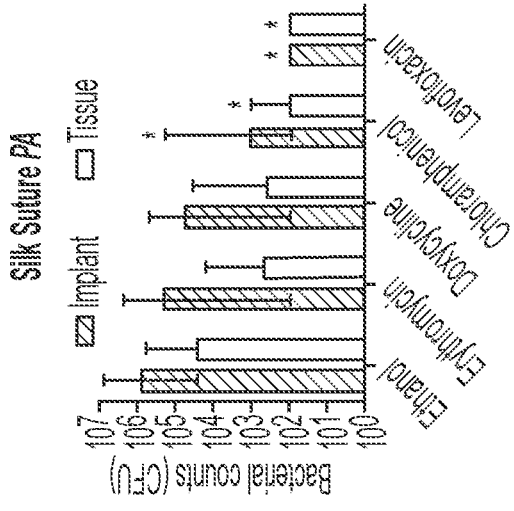
FIG. 5F

ANTIBIOTIC IMPLANT COATINGS AND PROCESS FOR MANUFACTURING IMPLANT COATINGS

CROSS-REFERENCE TO RELATED APPLICATIONS

This application is a § 371 U.S. National Stage Application of International Application No. PCT/US2018/057282 filed Oct. 24, 2018, and claims priority to U.S. provisional application No. 62/576,243 filed Oct. 24, 2017, the entire disclosures of which are incorporated herein by reference.

TECHNICAL FIELD

Embodiments of the present disclosure provide coatings for use on a variety of substrates, such coating being particularly useful for inhibiting implant associated infections, and processes for their manufacture.

BACKGROUND

Foreign body implantation can be found as a part of any surgical practice. Some of the most commonly implanted devices include artificial eye lenses, coronary stents, artificial knees, metal screws, pins and plates for traumatic repair, pacemakers and implantable cardiac defibrillators (ICD), breast implants, and vascular grafts. The incidence of wound infections associated with implantable medical devices in the era of antimicrobial prophylaxis is low, including 2.4% in orthopedic joint surgery, 11% in vascular surgery, 5.1% in breast implants, and <1% in ICDs. However, the morbidity caused when these infections occur can be high, causing readmission to the hospital, implant removal, amputations and even death. As such, wound infections associated with implanted foreign bodies remain a major source of potential morbidity for patients undergoing surgical procedures ranging from hernia repairs to major vascular surgery. These dreaded complications may necessitate the removal of the foreign body, additional major surgery, or prolonged recovery periods.

While many different methodologies have been employed to deal with the problem of implant-associated infections and other implant-associated complications, including antimicrobial washes, antibiotic loaded beads and sponges, and antimicrobial coated medical devices, there remains a persistent need in the art for new implant coatings and methods for producing the same. In particular, there remains a need in the art for coatings with demonstrated efficacy against implant-associated complications (e.g., coatings with with antimicrobial, antiplatelet, anti-coagulant, wound healing, and lubricating activities) and methods of producing the same.

SUMMARY

Accordingly, embodiments of the present disclosure provide novel coatings for implants and methods for making the coatings. Further provided are methods with demonstrated efficacy against implant-associated complications, including inhibiting of implant-associated infections against multiple species of bacterial cells.

One embodiment is directed to methods of applying a coating to a surface of a substrate, the methods comprising: providing a saturated or supersaturated solution of an an active compound in a fast-evaporating or medium-evaporating organic solvent; and coating the surface of the substrate with at least one application of the supersaturated solution, each application followed directly by a solvent evaporation period. In aspects, the active compound is an antimicrobial active, an antiplatelet active, a wound healing active, or a lubricating active. In particular aspects, the active compound is a small organic molecule. In aspects, the antimicrobial active is an antibiotic. In aspects, non-limiting examples of suitable antibiotics include, but are not limited to Doxycycline, Chloramphenicol, Erythromycin, and Levofloxacin. The use of a saturated or a supersaturated solution of an active compound in fast-evaporating or medium-evaporating solvents is critical to achieving a desired film architecture and film thickness; although means for enhancing evaporation may also be utilized when either fast evaporating or medium-evaporating solvents are used.

In aspects of methods for applying a coating to a surface of a substrate, providing a saturated or supersaturated solution of an active compound in a fast-evaporating or medium-evaporating organic solvent comprises admixing at least one active compound in a solvent of a fast-evaporating or medium-evaporating organic solvent to form a saturated or supersaturated solution. In aspects, providing a saturated or supersaturated solution of an active compound in a fast-evaporating or medium-evaporating organic solvent further comprises applying energy to the admixture to form a saturated or supersaturated solution.

In aspects of methods for applying a coating to a surface of a substrate, a solvent evaporation period comprises evaporating a portion of the solvent to organize the at least one active compound to form a coating comprising a self-assembled liquid crystalline mesophase material of the at least one active compound in solvent. In further aspects, a solvent evaporation period comprises evaporating a portion of the solvent to organize the at least one active compound to form a coating comprising a self-assembled liquid crystalline mesophase material of solvent in the at least one active compound. In even further aspects, a solvent evaporation period comprises evaporating a portion of the solvent to organize the at least one active compound to form a molecular crystal film coating.

Another embodiment of the present disclosure is directed to the novel coatings formed according to embodiments of the inventive processes. The coatings are distinguishable from coatings known in the art due to the evaporative-induced self-assembly of the active compound in the solvent upon deposition on the substrate surface and drying, at each round of coating, and the architecture and thickness thereby achieved. In aspects, the coatings formed comprise a self-assembled stable liquid crystalline mesophase material of the at least one active compound in solvent. In further aspects, the coatings formed comprise a self-assembled stable liquid crystalline mesophase material of solvent in the at least one active compound. In other aspects, the coatings formed comprise a molecular crystal film of the at least one active compound.

A further embodiment of the present disclosure is directed to medical devices coated with a coating formed from coating the device in a saturated or supersaturated solution of at least one active compound in hexane, acetone or ethanol, wherein coating comprises at least one step comprising coating followed directly by evaporating residual hexane, acetone or ethanol. In aspects, the coatings formed comprise a self-assembled stable liquid crystalline mesophase material of the at least one active compound in solvent. In further aspects, the coatings formed comprise a self-assembled stable liquid crystalline mesophase material of solvent in the at least one active compound. In other aspects, the coatings formed comprise a molecular crystal film of the at least one active compound. In aspects, the active compound is small organic molecule. In aspects, the active compound is an antimicrobial active, an antiplatelet active, a wound healing active, or a lubricating active. In aspects, the antimicrobial active is an antibiotic. In aspects, non-limiting examples of suitable antibiotics include, but are not limited to Doxycycline, Chloramphenicol, Erythromycin, and Levofloxacin.

Another embodiment is directed to medical devices coated with a coating formed from applying at least one coating to the device of a saturated or supersaturated solution of at least one active compound in acetone or ethanol, wherein a coating step is followed directly by evaporating residual acetone or ethanol. In aspects, the coatings formed comprise a self-assembled stable liquid crystalline mesophase material of the at least one active compound in solvent. In further aspects, the coatings formed comprise a self-assembled stable liquid crystalline mesophase material of solvent in the at least one active compound. In other aspects, the coatings formed comprise a molecular crystal film of the at least one active compound. In aspects, the active compound is a small organic molecule. In aspects, the active compound is an antimicrobial active, an antiplatelet active, a wound healing active, or a lubricating active. In aspects, the antimicrobial active is an antibiotic. In aspects, non-limiting examples of suitable antibiotics include, but are not limited to Doxycycline, Chloramphenicol, Erythromycin, and Levofloxacin.

Broadly, embodiments provide methods for preventing or inhibiting of implant associated complications, (e.g., implant associated infections) by coating the implant with a coating according to an embodiment of the invention as described in detail herein.

These and other embodiments and aspects will be further understood and clarified by reference to the figures and detailed description below. Although certain embodiments are illustrated and explained by specific examples, a person of ordinary skill in the art will understand that such examples should not be construed as limiting the full scope of the invention as set forth in the appended claims.

BRIEF DESCRIPTION OF THE FIGURES

FIGS. 2A-0 are images of antibiotic-coated implants. Pieces of PTFE, silk suture, or titanium screws were coated with Erythromycin (FIG. 2B, FIG. 2G, and FIG. 2L, respectively), Doxycycline Hyclate (FIG. 2C, FIG. 2H, and FIG. 2M, respectively), Chloramphenicol (FIG. 2D, FIG. 2I, FIG. 2N), or Levofloxacin (FIG. 2E, FIG. 2J, and FIG. 2O, respectively) as described in the Example section. Pieces were then analyzed with a Keyence optical camera at 100× (PTFE pieces and silk suture) and 50× (titanium screws) and compared to vehicle-coated pieces (FIG. 2A, FIG. 2F, and FIG. 2K). A color change is seen after coating PTFE with Doxycycline (FIG. 2C) and Levofloxacin (FIG. 2E). Changes to the gross appearance of the titanium screws are evident after coating with Erythromycin (FIG. 2L), Doxycycline (FIG. 2M), and Levofloxacin (FIG. 2O)

FIGS. 5A-F are graphical depictions demonstrating antibiotic coated implants prevent MRSA and *P. aeruginosa* Colonization in vivo. Silk suture (FIG. 5A and FIG. 5D), PTFE (FIG. 5B and FIG. 5E), and titanium screws (FIG. 5C and FIG. 5F) were coated with Erythromycin, Doxycycline, Chloramphenicol, and Levofloxacin as described in Example 1.2. They were then implanted into mice subcutaneously and contaminated with MRSA (FIGS. 5A-C) and *P. aeruginosa* (PA) (FIGS. 5D-F) as described in Example 1.5. Erythromycin, Doxycycline, Chloramphenicol, and Levofloxacin coating reduced MRSA colonization of silk suture in vivo by 5.1, 3.2, 1.2, and 5.1 log (FIG. 5A), respectively, colonization of PTFE in vivo by 3.8, 4.6, 3.1, and 4.5 log (FIG. 5B), respectively, and colonization of titanium screws in vivo by 2.2, 3.1, 2.2, and 3.3 log (FIG. 5C), respectively (n>9 per group, *=p<0.05). Erythromycin, Doxycycline, Chloramphenicol, and Levofloxacin coating reduced PA colonization of silk suture in vivo by 0.6, 1.2, 2.9, and 3.9 log (FIG. 5D), respectively, colonization of PTFE in vivo by 4.4 log each (FIG. 5E), and colonization of titanium screws in vivo by 0.5, 3.7, 3.7, and 4.0 log (FIG. 5F), respectively (n≤9 per group, *=p<0.05)

FIGS. 11C, F, and I are images were obtained with an iphone; FIGS. 11 A, D, G, and J were obtained using a transmission light microscope at 10× magnification; and FIGS. 11B, E, H, and K were obtained with a polarized light filter. FIGS. 11A-B are 100% ethanol (vehicle), FIGS. 11C-E are 1.9M palmitic acid (in 100% ethanol), FIGS. 11F-G are 1.6M stearlyamine (in 100% ethanol), and FIGS. 11I-K are 2.2M acetylsalicylic acid (in 100% ethanol).

FIG. 12A demonstrates that ODA/NAC and ODA/NAC/Abx coated tubes significantly reduced the amount of bacteria (>2 log) in the lungs of intubated pigs. FIG. 12B demonstrates that ODA/NAC/Abx coating significantly reduced the amount of adherent bacteria (>2 log) to the surface of endotracheal tubes. FIG. 12C shows that ODA/NAC and ODA/NAC/Abx significaty improved survival times of intubated pigs.

DETAILED DESCRIPTION

Figure 1D:
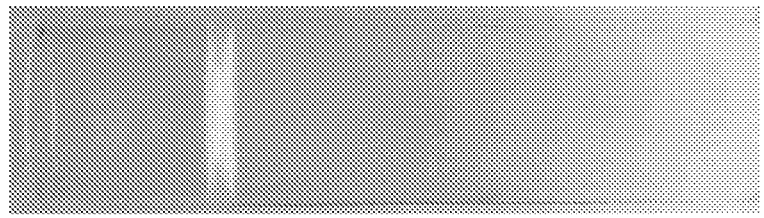
FIGS. 1A-D are images of supersaturated antibiotic-ethanol solutions. Supersaturated solutions of Doxycycline Hyclate (80 mM, 41 mg/mL) (FIG. 1A), Chloramphenicol (515 mM, 166 mg/mL) (FIG. 1B), Erythromycin (227 mM, 166 mg/mL) (FIG. 1C), and Levofloxacin (62 mM, 22 mg/mL) (FIG. 1D), were prepared by dissolving powdered Doxycycline Hyclate, Chloramphenicol, Erythromycin, and Levofloxacin, respectively, in 100% ethanol. The process involved heating the ethanol to 65° C. and slowly adding the solid solute under bath sonication and manual agitation until the resulting solution was transparent. The images of FIGS. 1A-D were taken immediately after glass vial was removed from the heated bath sonicator. No crystallization has occurred in solution, but objects dip coated in such supersaturated solutions will acquire a coating comprising a self-assembled stable liquid crystalline mesophase material of the antibiotic in ethanol, a coating a self-assembled stable liquid crystalline mesophase material of ethanol in the antibiotic, or a molecular crystal film coating of antibiotic, depending on the amount of evaporation of the ethanol from the coating.
Figure 1C:
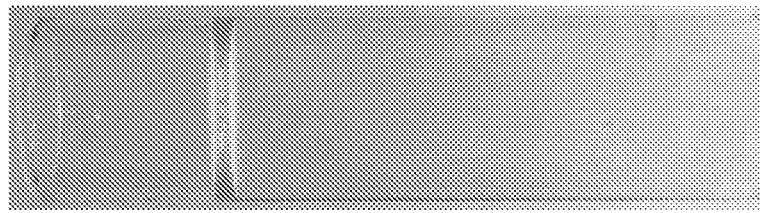
Figure 1B:
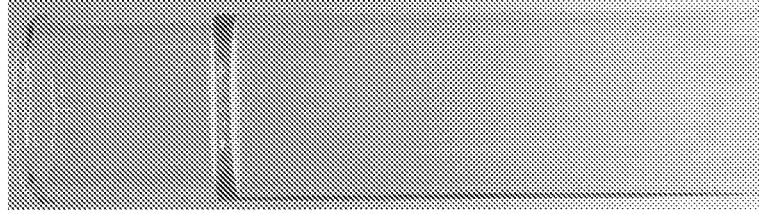
Figure 1A:
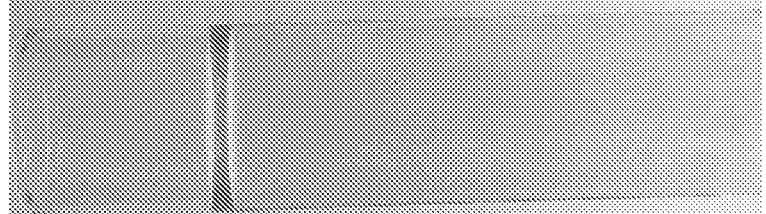

Embodiments of the present disclosure provide saturated or supersaturated coating solutions of at least one active compound dissolved in a fast-evaporating or medium-evaporating solvent, and novel coating processes, and novel coatings that may be applied to a variety of substrates to substantially prevent or inhibit implant-associated complications (e.g., implant associated microbial infections). In aspects, the active compound a small organic molecule. In aspects, the active compound is an antimicrobial active, an antiplatelet active, a wound healing active, or a lubricating active. In aspects, the antimicrobial active is an antibiotic. In aspects, non-limiting examples of suitable antibiotics include, but are not limited to Doxycycline, Chloramphenicol, Erythromycin, and Levofloxacin. The instantly-disclosure provides novel methods of applying clinically relevant amounts of an active compound to the surface of implantable medical devices through the use of saturated or supersaturated coating solutions of at least one active compound dissolved in a fast-evaporating or medium-evaporating solvent and demonstrates its effectiveness when using antibiotic coatings on PTFE, silk suture, and titanium screws in a murine subcutaneous model of infection. The coating method is a cheap, effective, and an easily scalable way to create an implantable foreign body that addresses implant-associated complications, such as a scalable way to create an implantable foreign both that is resistant to bacterial colonization and infection.

This concept can be applied to other bioactive molecules, besides antibiotics, and other surfaces in the formation of molecular crystal films. Molecular crystals are a diverse class of structures that can be composed of polymers or organic small molecules. Polymer molecular crystals are very well characterized and are ubiquitous in our daily life. They exist as paints, anti-reflective coatings on sunglasses, or non-stick coatings on our pans. Small molecule molecular crystal films are rarer. They have been well described as subjects of research in optoelectronics, but are not seen in daily use.

Formation of these active compound-containing film coatings can be explained by various physical forces acting in concert to promote crystallization. As described above, the instantly-disclosed methods begin with a saturated or supersaturated solution of an active compound (e.g., any given antibiotic) in fast-evaporating or medium-evaporating organic solvents (e.g., but not limited to, 100% ethanol). For example, it is herein reported a solubility of Doxycycline Hyclate in 100% ethanol of 41 mg/mL. This supersaturated solution is the highest reported concentration in ethanol and is likely near its maximum. The method subsequently involves applying the solution to the substrate surface, e.g., by performing a dip coating process using this supersaturated solution stock.

Classically, the process of dip coating has been explained by immersion, dwell time, deposition and drainage, and solvent evaporation. Substrates of interest are immersed in the precursor solution, dwell for a defined period of time, and are withdrawn at a constant speed (e.g., but not limited to, 200 mm/s) resulting in a thin layer of entrained precursor solution deposited on the surface. As the substrate exits the precursor solution evaporation of the solvent occurs. The behavior of the dissolved molecule of interest (i.e., active compound) during solvent evaporation is unique. It is not only specific to the molecule of interest, but also to the molecule solvent interactions and molecule, solvent, surface, interactions. The present investigators have found that for many small organic molecules (including antibiotics such as, but not limited to, Erythromycin, Doxycycline, Chloramphenicol, and Levofloxacin) at saturated and supersaturated concentrations (often approaching and even exceeding, maximum reported solubility in volatile organic solvents (including ethanol)), the rapid cooling and evaporation of the solvent in the entrained fluid film formed by dip coating further concentrates the solution and results in crystallization of the small organic molecules in films that vary in thickness (e.g., <1 µm to 200 µm).

A related phenomena has been characterized where silica was combined with high concentrations of surfactant resulting in well-ordered three dimensional mesophases (Yang H, Kuperman A, Coombs N, Mamiche-Afara S. Synthesis of oriented films of mesoporous silica on mica—ProQuest. Nature. 1996, herein incorporated by reference in its entirety). Brinker et al. advanced this concept and coined the term evaporation induced self-assembly (EISA) (Brinker C J, Lu Y, Sellinger A, Fan H. Evaporation-induced self-assembly: nanostructures made easy. Adv Mater. 1999, herein incorporated by reference in its entirety). They have developed several biological applications for this process. They take advantage of the phase changes of surfactants in which they progress from individual molecules in solution to micelles, and then well-ordered three-dimensional mesophases as the concentration is increased. These mesophases have primarily been studied with water as the solvent, but they also occur in organic solvents such as ethanol. The process of the instant disclosure differs from Brinker's in that it does not involve the addition of inorganic materials, does not utilize water as a co-solvent, and utilizes a small organic molecule not generally classified as a surfactant. However, since many active compounds (e.g., antibiotics such as doxycycline) have hydrophobic and hydrophilic domains, they can also form mesophases at high concentrations. Thus, the instantly-disclosed methods that start with saturated or supersaturated solutions of the active compound and subsequent coating is performed (e.g., by dip coating). Evaporation of the solvent in the entrained film forms a stable three-dimensional mesophase of the active compound (e.g., antibiotic) in solvent (e.g. ethanol). Continued evaporation of the solvent in the entrained film forms a stable reverse mesophase of solvent in the active compound. Even further evaporation of the solvent from the entrained film, such as the solvent evaporation period being sufficient for substantially complete evaporation of solvent, results in the formation of a stable molecular crystal thin film of the active compound (e.g. a stable molecular crystal thin film of antibiotic).

According to one embodiment, methods for applying coating to a surface of a substrate are provided. In aspects, a method for applying a coating to a surface of a substrate comprises a) providing a saturated or supersaturated solution of an active compound (e.g. antibiotic) in a fast-evaporating or medium-evaporating organic solvent; and b) coating the surface of the substrate with at least one application of solution, each application followed directly by a solvent evaporation period.

A "substrate" may be any substrate on which it is desirable to apply the coatings of the instant disclosure. Non-limiting examples of suitable substrates include substrates such as polymeric materials, plastics (e.g., polyvinyl chloride), textiles, glass, silicone, metals (e.g. aluminum), other natural or synthetic materials. Particular substrates of interest include the surface of an implant. As is known in the art, implants may be formed from a variety of biocompatible materials. The most common materials include titanium. Titanium alloys may also be used as implant materials. An example of a titanium alloy is an alloy of titanium alloyed with 6% aluminum and 4% vanadium. Other materials such as stainless steel, nickel-chromium alloys, nickel-chromium-cobalt alloys may be used. Implants may also be formed from biocompatible polymeric materials. Examples of polymeric materials include, but are not limited to, polytetrafluoroethylene (PTFE), ultra-high molecular weight polyethylene, polylactic acid, and polyglycolic acid. Although aspects of the invention are discussed and exemplified using specific substrates, it will be readily apparent to a person of ordinary skill in the art that any surface of an implant on which the prevention or inhibition of implant-associated microbial infections is sought may be a suitable substrate.

In aspects, the active compound can include any physiologically or pharmacologically active substance that produces a localized or systemic effect in a patient. In aspects, the active compound can be selected from antibiotics, antiviral agents, anepileptics, analgesics, anti-inflammatory agents and bronchodilators, and may be inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable active compounds may be selected from, for example, polysaccharides, steroids, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

In aspects, the active compound is an antimicrobial active, an antiplatelet active, a wound healing active, or a lubricating active. In aspects, examples of an active compound include Acetaminophen, Acetylsalicylic acid, Acrylamide, Ascorbic Acid, Bacitracin, Benzocaine, Chloramphenicol, Chlorhexidine, Cholic Acid, Citric Acid, Doxycycline Hyclate, Erythromycin, Glyceryl trioleate, Lauric Acid, Levofloxacin, Lidocaine, Myristic Acid, N-Acetyl-L-Cysteine, Neocuproine, Octadecylamine, Palmitic Acid, Phosphatidylcholine, Phosphatidylserine, Probenecid, Rifampicin, Salicylic acid, Stearic Acid, Sulfamethoxazole, Trimethoprim, Triclosan, Urea, Vanillin, and Warfarin. In aspects, the antimicrobial active is an antibiotic.

"Antibiotics" include, but are not limited to, compositions selected from the group consisting of Gentamicin, Kanamycin, Neomycin, Netilmicin, Tobramycin, Paromomycin, Spectinomycin, Geldanamycin, Herbimycin, Rifaximin, Streptomycin, Ertapenem, Doripenem, Imipenem/Cilastatin, Meropenem, Cefadroxil, Cefazolin, Cephalothin, Cephalexin, Cefaclor, Cefamandole, Cefoxitin, Cefprozil, Cefuroxime, Cefixime, Cefdinir, Cefditoren, Cefoperazone Cefotaxime, Cefpodoxime, Ceftazadime, Ceftibuten, Ceftizoxime Ceftriaxone, Cefepime, Ceftaroline fosamil, Ceftobiprole, Teicoplanin, Vancomycin, Telavancin, Daptomycin, Oritavancin, WAP-8294A, Azithromycin, Clarithromycin, Dirithromycin, Erythromycin, Roxithromycin, Telithromycin, Spiramycin, Clindamycin, Lincomycin, Aztreonam, Furazolidone, Nitrofurantoin, Oxazolidonones, Linezolid, Posizolid, Radezolid, Torezolid, Amoxicillin, Ampicillin, Azlocillin, Carbenicillin, Cloxacillin Dicloxacillin, Flucloxacillin, Mezlocillin, Methicillin, Nafcillin, Oxacillin, Penicillin G, Penicillin V, Piperacillin, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Mafenide, Sulfacetamide, Sulfadiazine, Sulfadimethoxine, Sulfamethizole, Sulfamethoxazole, Sulfasalazine, Sulfisoxazole, Trimethoprim-Sulfamethoxazole, Sulfonamidochrysoidine, Demeclocycline, Doxycycline, Vibramycin Minocycline, Tigecycline, Oxytetracycline, Tetracycline, Clofazimine, Capreomycin, Cycloserine, Ethambutol, Rifampicin, Rifabutin, Rifapentine, Arsphenamine, Chloramphenicol, Fosfomycin, Fusidic acid, Metronidazole, Mupirocin, Platensimycin, Quinupristin/Dalfopristin, Thiamphenicol, Tigecycline and Tinidazole and combinations thereof. In aspects, the antibiotic of the instant methods and coatings is selected from one or more of Doxycycline, Chloramphenicol, Erythromycin, and Levofloxacin.

A solvent according to embodiments of the present disclosure includes any organic solvent with a fast evaporation rate, and some solvents with a medium evaporation rate when subjected to evaporation enhancing/drying conditions. Evaporation rate is the rate at which a material will vaporize (evaporate, change from liquid to vapor) compared to the rate of vaporization of a specific known material under ambient conditions. This quantity is a ratio; therefore it is unitless, but is based on an n-butyl acetate standard=1. A fast-evaporating solvent, as the term is utilized herein, conforms to a conventional industry definition as one with an evaporation rate of 3.0 (three time the evaporation of normal butyl acetate), such as acetone (5.6), hexane (8.3), or methyl ethyl ketone or MEK (3.8). Chemicals with evaporation rate between 0.8 and 3.0, based on an n-butyl acetate standard=1, such as ethanol (1.4) or VM&P naphtha (1.4), methanol, and ethyl acetate are classified as medium-evaporating. Chemicals with evaporation rates less than 0.8, such as water (0.3), mineral spirit (0.1), or xylene (0.6) or isobutyl alcohol (0.6) are classified as slow evaporating and are not contemplated as within the scope of the invention. In aspects, the rapid evaporation of the solvent subsequent to a coating step is critical to achieving the desired antibiotic coating architecture. In aspects, preferred organic solvents are therefore those with a standard evaporation rate greater than 3. According to specific aspects, the fast-evaporating solvent is selected from one or more of hexane, acetone, cyclohexane, and methyl ethyl ketone. In other aspects, organic solvents are therefore those with a standard evaporation rate between 0.8 and 3.0. According to specific aspects, the medium-evaporating solvent is selected from one or more of ethanol, naphtha, methanol, and ethyl acetate. In specific aspects, the solvent is 95%, 96%, 97%, 98%, 99%, or 100% ethanol. In very specific embodiments, the antibiotic is selected from one or more of Doxycycline, Chloramphenicol, Erythromycin, and Levofloxacin and the solvent comprises ethanol.

According to some aspects, providing a saturated or supersaturated solution of an active compound (e.g. an antibiotic) in a fast-evaporating or medium-evaporating organic solvent comprises admixing an active compound in a solvent of a fast-evaporating or medium-evaporating organic solvent to form a saturated or supersaturated solution. In aspects, providing a saturated or supersaturated solution of an active compound in fast-evaporating or medium-evaporating organic solvent further comprises applying energy to the admixture to form a saturated or supersaturated solution. Energy may be in the form of mechanical energy, sonication, heating, and combinations thereof. In specific embodiment, a probe or bath sonicator is employed. In very specific embodiments the sonicator is employed at ultrasonic frequencies, and in other specific embodiments the sonication frequency is between 20 kHz and 40 kHz. According to some specific embodiments the temperature of a bath sonicator is set to at least 5-10° C. below the selected solvent's boiling point. In very specific embodiments the temperature of the bath is set at about 5° C. below the solvent's boiling point. Heating is to a temperature less than the solvent's boiling point. According to more specific embodiments, the solution is heated to within 10° C. of the solvent boiling point and sonicated at about 40 kHz. The resultant saturated or supersaturated solution provides the coating solution.

Desired substrates are coated by the saturated or supersaturated solution of an active compound (e.g. an antibiotic) in a fast-evaporating or medium-evaporating organic solvent by any suitable coating methods including any method which employs rapid evaporation of solvent, for example, spray coating, spin coating, and dip coating. Without being bound by theory, the present investigators surmise that the self-assembly of the active compound on the surface of the substrate is guided by the solvent and rapid evaporation freezes the resultant architecture in place. A single coating may be effective for preventing implant-associated complications, including implant-associated infections; however in some embodiments durability and sustained efficacy may be enhanced by multiple coatings. Thus, according to some embodiments, the surface of the substrate is coated with at least one application of solution, each application followed directly by a solvent evaporation period. As utilized herein, an "application cycle" includes both a coating step and an evaporation step. An evaporation step results in substantially complete evaporation of residual solvent. Evaporation is substantially complete if the coated substrate is dry to the touch. According to other embodiments, at least ten application cycles are provided. In other specific embodiments, 2, 3, 4, 5, 6, 7, 8, 9, or 10 application cycles are provided. The number of application cycles may vary by the specific combination of active compound and solvent, the drying conditions if on-site, by quality of the substrate, and by the intended environment/use of the coated substrate.

According to some aspects, the evaporation rate of fast-evaporating or medium-evaporating solvents (such as the medium-evaporating solvent ethanol), may be enhanced, such as by air drying, blow-drying, vacuum-drying or heat-assisted drying, with retention of desired coating properties. According to aspects, the active compound is an antibiotic, and the antibiotic is selected from one or more of Doxycycline, Chloramphenicol, Erythromycin, and Levofloxacin and the solvent comprises ethanol (e.g., 95%, 96%, 97%, 98%, 99%, or 100% ethanol). In other aspects, the active compound is one or more of Acetaminophen, Acetylsalicylic acid, Acrylamide, Bacitracin, Benzocaine, Chloramphenicol, Chlorhexidine, Cholic Acid, Citric Acid, Doxycycline Hyclate, Erythromycin, Glyceryl trioleate, Lauric Acid, Levofloxacin, Lidocaine, Myristic Acid, N-Acetyl-L-Cysteine, Neocuproine, Octadecylamine, Palmitic Acid, Phosphatidylcholine, Phosphatidylserine, Probenecid, Rifampicin, Salicylic acid, Stearic Acid, Sulfamethoxazole, Trimethoprim, Triclosan, Urea, Vanillin, and Warfarin, and the solvent comprise ethanol (e.g., 95%, 96%, 97%, 98%, 99%, or 100% ethanol). In other aspects, the active compound is Ascorbic Acid and the solvent comprise methanol (e.g., 95%, 96%, 97%, 98%, 99%, or 100% methanol). In aspects, the coated substrate is brought to ambient temperature such that the solvent evaporation period takes place substantially at room temperature. In other aspects, the coated substrate is subject to blow-drying and/or elevated temperature during the evaporation aspect of the coating cycles. The evaporation rate of organic solvents is a well-known parameter and may be readily ascertained by reference to, for example, Handbook of Organic Solvent Properties, Halsted Press as an imprint of John Wiley & Sons Inc., 605 Third Avenue, New York, N.Y. 10158, Smallwood, 1996, the entire disclosure of which is incorporated herein.

In aspects, the solvent evaporation period is sufficient for evaporation to solvent to form a stable liquid crystalline mesophase material of the at least one active compound (e.g. antibiotic) in solvent. In other aspects, the solvent evaporation period is sufficient for evaporation to solvent to form a stable liquid crystalline mesophase material of solvent in the at least one active compound. In further aspects, the solvent evaporation period is sufficient for substantially complete evaporation of solvent to form an molecular crystal film coating of the active compound.

Another embodiment of the present disclosure is directed to the coatings formed from embodiments of the instantly-disclosed processes. Morbidity caused by infections associated with implanted medical devices continues to be high, causing readmission to the hospital, implant removal, amputations and even death. Embodiments of the evaporative-induced deposition of an active compound (e.g., antibiotics) via dip coating provide a simple and cheap way to apply a biologically significant amount of active compound on the surface of implants. According to some method embodiments, only a single dip is required and thus only a very small volume of a saturated or supersaturated solution of active compound is used.

The following Examples establish that implants coated by the instantly-disclosed processes, as well as the antibiotic coatings produced by such processes, are highly efficacious at treating and/or preventing bacterial infections (e.g., but not limited to, *S. aureus* (MRSA), and *P. aeruginosa*).

EXAMPLES

The following examples are intended to illustrate specific features and aspects of the instant-disclosure and should not be construed as limiting the scope thereof.

Example 1

Materials and Methods

Example 1.1

Materials and Mice

Doxycycline Hyclate (D9891), Chloramphenicol (C0378), Erythromycin (E5389), and Levofloxacin (28266) were purchased from Sigma-Aldrich (St. Louis, Mo.). Absolute, 200 proof, molecular biology grade ethanol was purchased from Fisher Scientific (Pittsburgh, Pa.). (PTFE) vascular grafts were obtained from expired stock at W.L. Gore and associates. Experimental 2-0 and 3-0 silicone treated non-absorbable silk suture was manufactured by Sherwood Davis & Geck, a division of Medtronic. Titanium screws were loaned from KLS Martin Group. Trypticase soy broth (TSB) agar plates and TSB agar plates with 5% sheep's blood were obtained from BD Biosciences. Male, 8 week old, CF-1 mice were obtained from Charles River Laboratories (Wilmington, Mass.).

Example 1.2

Antibiotic Stock Solution Preparation and Molecular Crystal Thin Film Coating

Exemplary supersaturated solutions of Doxycycline Hyclate (80 mM, 41 mg/mL), Chloramphenicol (515 mM, 166 mg/mL), Erythromycin (227 mM, 166 mg/mL), and Levofloxacin (62 mM, 22 mg/mL) were prepared by dissolving powdered Doxycycline Hyclate, Chloramphenicol, Erythromycin, and Levofloxacin in 100% ethanol. The process involved heating the ethanol to 65° C. and slowly adding the solid solute under bath sonication and manual agitation until the resulting solution was transparent. Dip coating was then carried out at room temperature immediately after removing the stock solutions from the heated water bath.

Intact 5 cm sections of PTFE graft, full 75 cm length of silk suture, and individual titanium screws were dip-coated into each antibiotic solution and immediately withdrawn at a rate of ~200 mm/s. Thin films of antibiotic were subsequently formed as the ethanol evaporated.

The resultant films were not polymers (held together by covalent or ionic bonds) but rather molecular crystal films (held together by rather weak molecular forces such as Van Der Waals and hydrophobic forces). As the solvent evaporated, the concentration of the molecule of interest rapidly increased, favoring crystallization. Due to the rapid nature of the crystallization process, however, a stable metaphase was captured, physically represented as a film. After a first portion of the solvent is evaporated, a first stable metaphase includes a self-assembled stable liquid crystalline mesophase material of the antibiotic (e.g., Doxycycline, Chloramphenicol, Erythromycin, or Levofloxacin) in solvent (e.g., ethanol). After a further portion of the solvent is evaporated, a second stable metaphase includes a self-assembled stable liquid crystalline mesophase material of solvent (e.g., ethanol) in the antibiotic (e.g., Doxycycline, Chloramphenicol, Erythromycin, or Levofloxacin). After even a further portion of the solvent is evaporated, the coatings formed comprise a molecular crystal film of the antibiotic (e.g., Doxycycline, Chloramphenicol, Erythromycin, or Levofloxacin).

After the PTFE, silk suture, and titanium are withdrawn from the antibiotic stock solution, they were allowed to further dry overnight at ambient conditions at room temperature. Vehicle (100% ethanol)-coated pieces were prepared in an identical manner, substituting absolute ethanol for the antibiotic stock solutions. PTFE implants were then cut to 5 mm×5 mm pieces, and silk suture was cut to 2 cm length for use in vitro and in vivo. Titanium screws were not further manipulated prior to use in vitro and in vivo.

Example 1.3

Bacterial Strains and Media

Clinical strains of methicillin resistant *S. aureus* (MRSA), and *P. aeruginosa* (strain 762) were used. MRSA was obtained from the clinical microbiology lab of Shriner's Hospital for Children (Cincinnati, Ohio). *P. aeruginosa* 762 was obtained from the Department of Microbiology University Hospital Essen (Essen, Germany). *P. aeruginosa* was grown from frozen glycerol stock overnight on TSB agar plates. MRSA was grown overnight from frozen glycerol stock on TSB agar plates with 5% sheep's blood. Bacteria were prepared for subcutaneous implant infection and in vitro testing by first transferring bacteria from the plate to warmed TSB at 37° C. agitated at 125 RPM to induce a logarithmic growth phase. Bacteria were then washed twice by centrifugation at 3000×g for 10 min and resuspension in 0.9% NaCl. The optical density of the suspended bacteria was determined at 550 nm light and final inoculating concentration calculated from standard curves specific to each strain. Bacteria remained in 0.9% NaCl for in vivo testing but were placed back into TSB for in vitro testing.

Example 1.4

In Vitro Bacterial Adherence and Colonization

Small pieces of PTFE (5 mm×5 mm), silk suture (2 cm), and titanium screws antibiotic-coated and vehicle (100% ethanol)-coated, were prepared for analysis as in Example 1.2. Bacteria was prepared as in 2.3 and 1000 colony forming units (cfus) in 300 µL was placed in the wells of 96-well plates. The antibiotic-coated and vehicle-coated pieces were then immersed and incubated for 24 hours at 37° C., 95% humidity (n=15 per group). Pieces were then placed in 10 mL sterile PBS and bath sonicated for 10 minutes to release adherent bacteria. Bacteria were quantified by the plate dilution method.

Example 1.5

Subcutaneous Implant and Infection of Mice

CF-1 mice were anesthetized with 120 mg/kg ketamine/16 mg/kg xylazine injected intraperitoneally and their backs shaved with electric clippers. A 2 cm incision was made in the back and implants (5 mm×5 mm PTFE, 2 cm silk suture, or titanium screws) were placed subcutaneously (n=9 per group). Bacterial suspensions (2.5 million cfu in 100 µL for MRSA and 2 million cfu in 100 µL for *P. aeruginosa*) prepared as described in Example 1.2 were then injected into the subcutaneous space and the wound closed with 3-0 silk suture.

Example 1.6

Bacterial Quantification

Mice were sacrificed 3 days post infection. The implant capsule was entered with sterile instruments and the implant was removed and placed in 10 mL of sterile PBS. Tissue from the inferior wall of the implant capsule was excised and placed in 10 mL sterile PBS. The implants and tissue were placed in a bath sonicator for 10 min to release adherent bacteria. Bacteria were then quantified by the plate dilution method. The most concentrated solution plated for each sample was a 1:100 dilution. Any empty plate was recorded as 1 cfu and, thus, the lowest value recorded was 100 CFU.

Example 1.7

Tissue Fixation and Histology

Mice designated for histological analysis underwent identical subcutaneous implant placement and infection as described in Example 1.3. Additional mice also underwent subcutaneous implant placement without infection as controls. After post implant day 7, mice were sacrificed and the skin, implant, and implant capsule were excised en bloc and fixed in 4% formaldehyde. Tissues were processed and embedded in paraffin. Tissue sections were then obtained and underwent hematoxylin and eosin (H&E) staining. Immunohistochemistry was performed for rat anti-Ly-6 C/G (BD Pharmingen, 550291), a neutrophil marker. Tissue sections were deparaffinized, rehydrated and blocked with 10% fetal bovine serum (FBS). Epitope retrieval was performed via incubation with Pepsin Digest-all 3 (Invitrogen 003009) at 37° C. for 30 min. The secondary antibody used was Alexa Fluor goat anti-rat IgG (H+L) (Molecular Probes A11006). H&E stained slides were analyzed via light microscopy (ZEISS Axiostar plus transmitted light microscope). Immunohistochemistry slides were analyzed via confocal fluorescent microscopy (Nikon A1R GaAsP inverted microscope).

Example 1.8

Materials Characterizations

Material characteristics of the vehicle coated and antibiotic coated PTFE and silk suture samples were evaluated using various techniques. A digital microscope (Keyence, VHX-1000) was used to examine and image the surface of implants before and after coating. Even though some antibiotic films can be easily seen with microscopy, the presence of the antibiotics on implant surfaces was confirmed by Fourier Transform Infrared spectroscopy (FTIR) (Thermo Scientific, Nicolet 6700). FTIR spectra were collected directly from implant surfaces by using the Smart Orbit diamond ATR module (Thermo Scientific). An ellipsometer (J. A. Woollam, Vase) was used in order to estimate the proximate thickness of the antibiotics films on the implants. Since this technique doesn't allow direct measurement of film thickness on PTFE and silk suture, we prepared antibiotic films on glass slides under identical conditions. It was assumed that the thicknesses we measured on glass slides will be close to the thicknesses on the implant surfaces.

Mass of antibiotic on implant was determined by measuring the weight of each implant piece before and after coating. An analytical microbalance (Mettler Toledo, Model MT5) was used for weight measurements. For electron microscopy, sample segments were mounted on standard aluminum specimen mounts using carbon conductive tape. Mounted segments were then sputter coated with 10 nm gold/palladium and imaged using scanning electron microscopy (SEM) (FEI/Phillips XL-30 SEM).

Example 1.9

Implantation of Coated Endotracheal Tubes in Pigs

Adult female pigs were anesthetized and incubated with either uncoated, Octadecylamine (ODA)/N-acetyl cysteine (NAC) coated, or ODA/NAC/doxycycline+levofloxacin (Abx) coated tubes and mechanically ventilated under sedation for up to 72 hours. The combination coating solutions were prepared to a total volume of 250 cc with ethanol as the solvent. The final concentrations of the active molecules were 1.2 M Octadecylamine, 50 mM Doxycycline Hyclate, 50 mM Levofloxacin, and 72 mM N-acetyl-cysteine. The endotracheal tubes were coated by the following procedure. The stock concentrations were heated to 70° C. and then placed in a 250 cc graduated glass cylinder. The endotracheal tubes were warmed to 70° C., and dip coating was performed. The tubes were immersed into the cylinder slowly and once the tube is completely immersed, it is withdrawn at a rate of 1 cm/sec. The tubes were allowed to cool at room temperature for 10 minutes. The dip coating and cooling processes were repeated. The tubes were then vacuum sealed for storage until use. Portions of the lungs (right upper lobe (RUL), right lower lobe (RLL), left upper lobe (LUL), and left lower lobe (LLL)) and trachea were harvested after the pigs either died, or were sacrificed at the study endpoint (72 hours). Lungs were homogenized and bacteria quantified in the homogenate by the plate dilution method. Trachea and endotracheal tube pieces were placed in neutralizing broth and immersed in a sonicating bath for 10 min to release adherent bacteria. Bacteria were quantified with the plate dilution method.

Example 1.10

Statistical Methods

The primary endpoint used for the in vivo subcutaneous infection was bacterial colony forming units (CFUs) adherent to the implant. In order to perform an a priori power analysis for a two-sided t-test, it was expected at least a 50% reduction of bacteria with our coated implants compared to controls. A standard deviation of 40% of the mean of the controls was expected. We can accept alpha=0.05 for the probability of committing a Type I error and a beta=0.2 for the probability of committing a Type II error (Power of 0.8). With these parameters, we require a sample size of 6 mice per group. Mean bacterial CFUs were reported +/−standard deviation. Mean counts from implants and tissues were compared using Student's t test.

Example 2

Results

Example 2.1

Erythromycin, Doxycycline Hyclate, Chloramphenicol, and Levofloxacin were Prepared to Concentrations Higher than Previously Reported (e.g., Supersaturated Solutions) in Ethanol Using Heat and Sonication As seen in FIGS. 1A-D, supersaturated solutions were prepared as described in Example 1.2. Supersaturated solutions of Doxycycline Hyclate (e.g., 80 mM, 41 mg/mL) (FIG. 1A) resulted in a green tinted transparent solution, supersaturated solutions of Erythromycin (e.g., 227 mM, 166 mg/mL) (FIG. 1C) and Chloramphenicol (e.g., 515 mM, 166 mg/mL) (FIG. 1B) were clear/yellow transparent, and supersaturated solutions of Levofloxacin (e.g., 62 mM, 22 mg/mL) (FIG. 1D) were yellow/green tinted transparent. The reported solubility in the literature of the above antibiotics in ethanol are incompletely studied. Doxycycline Hyclate is reported to be sparingly soluble in alcohol. Chloramphenicol is well known to be soluble in ethanol. Sigma reports an ethanol solubility of 50 mg/mL. Erythromycin is also reported to be freely soluble in ethanol and Sigma also reports an ethanol solubility of 50 mg/mL. Levofloxacin has been reported to be soluble in ethanol with Abcam reporting solubility up to 10 mM. It is herein reported higher solubilites in ethanol than have been previously reported for these four antibiotics. The process of sonication, in addition to temperatures near the boiling point of the solvent, ethanol, likely contribute to this effect of forming supersaturated solutions. Previous research investigating the effect of sonochemistry on solubility hypothesize that the cavitation bubbles create localized "hot spots" in which supercritical fluid (SCF) resides. Solubilities are increased in this SCF and remain even after the "hot spots" dissipate into the bulk solution (Thompson L H, Science LDCE, 2000. The rate enhancing effect of ultrasound by inducing supersaturation in a solid-liquid system. Elsevier. doi:10.1016/S0009-2509(99)00481-9, herein incorporated by reference in its entirety).

Example 2.2

Figure 3:
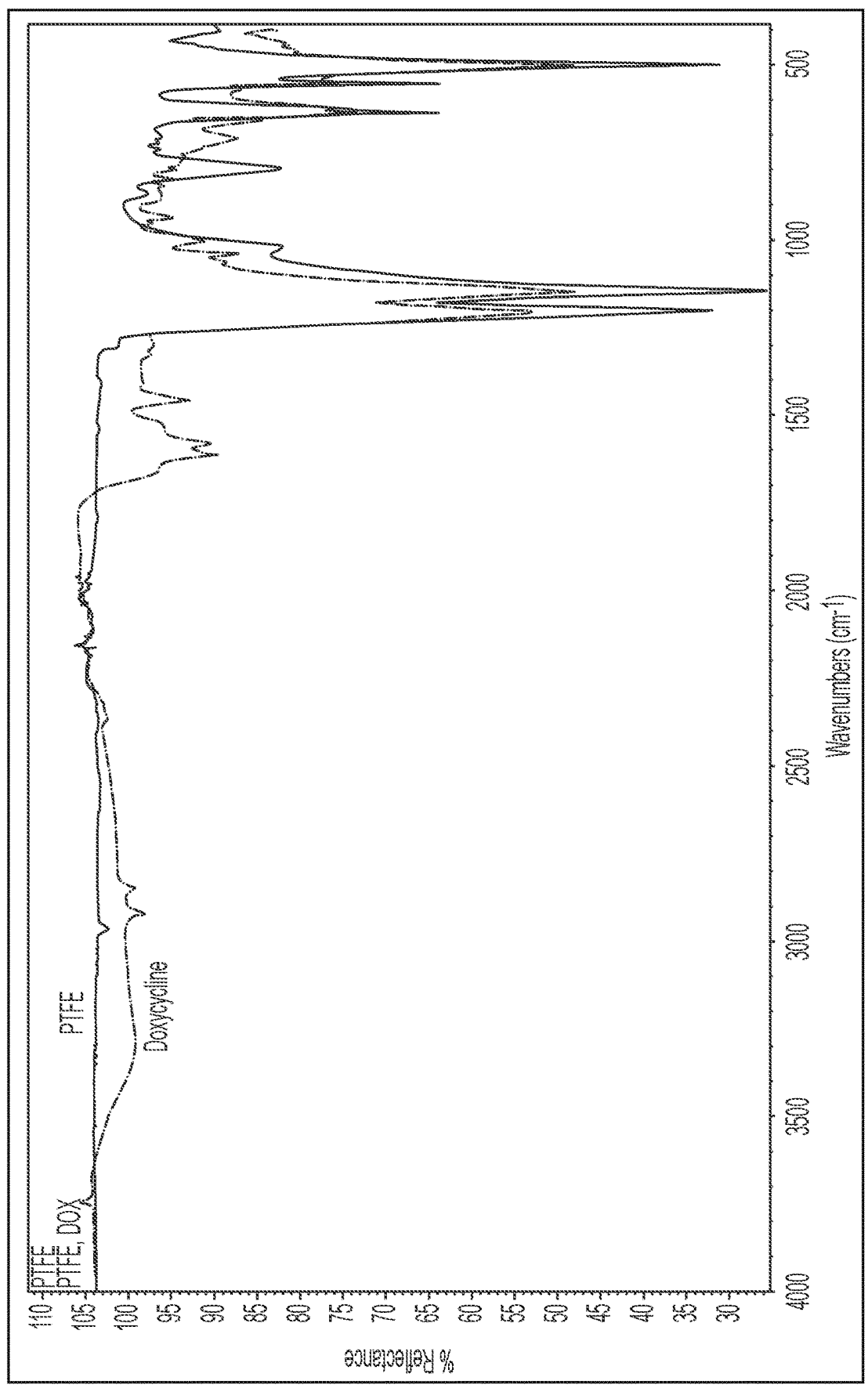
FIG. 3 is a graphical depiction of a FTIR Spectra of Pristine PTFE and Doxycycline Coated PTFE. Broad peak at 3400 cm-1 is due to the stretching of multiple —OH groups. Double peaks 1612 cm-1 and 1580 cm-1 indicate two indicate the carbonyl groups. Single peak at 1455 cm-1 is indicative of an amide carbonyl group.
Figures 4A, 4B, 4C:
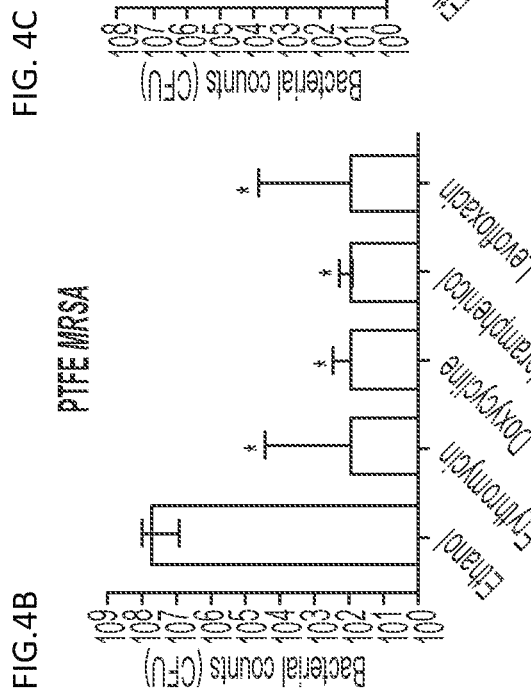
FIG. 4A-F are graphical depictions demonstrating antibiotic coated implants prevent MRSA and *P. aeruginosa* colonization in vitro. Silk suture (FIG. 4A and FIG. 4D), PTFE (FIG. 4B and FIG. 4E), and titanium screws (FIG. 4C and FIG. 4F) were coated with Erythromycin, Doxycycline, Chloramphenicol, and Levofloxacin as described in Example 1.2. Pieces were then incubated with MRSA (FIGS. 4A-C) and *P aeruginosa* (PA) (FIGS. 4D-F) as described in section Example 1.4. Erythromycin, doxycycline, chloramphenicol, and levofloxacin coating significantly reduced MRSA adherent to silk suture by 5.2 log each (FIG. 4A), adherent to PTFE by 5.7 log each (FIG. 4B), and adherent to titanium screws by 5.2 log each (FIG. 4C) compared to vehicle (100% ethanol)-coated controls (n≥15 per group, *=p<0.05). While doxycycline and levofloxacin significantly reduced PA adherent to silk suture 6.0 log each (FIG. 4D), adherent to PTFE by 6.1 log each (FIG. 4E), and adherent to titanium screws by 6.4 log each (FIG. 4F), compared to vehicle-coated controls (n≥15 per group, *=p<0.05). Additionally, erythromycin significantly reduced adherence of PA to PTFE and titanium screws (FIG. 4E and FIG. 4F) and chloramphenicol significantly reduced PA adherence to silk suture and PTFE (FIG. 4D and FIG. 4F) (n>15 per group, *=p<0.05).
Figures 4D, 4E, 4F:
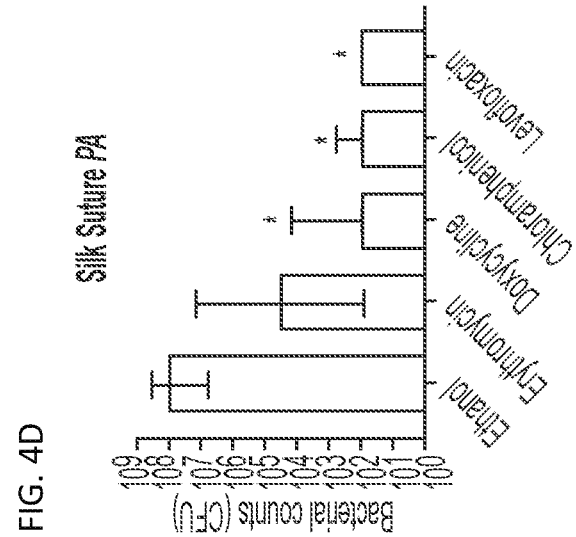

Antibiotic Coating Increases Mass and May Change the Color, But Does Not Alter the Gross Appearance of Implant As seen in FIGS. 2A-O, dip coating in Doxycycline Hyclate (FIG. 2C, FIG. 2H) causes a color change from white to pale green. Erythromycin (FIG. 2B and FIG. 2G), chloramphenicol (FIG. 2D and FIG. 2I), and Levofloxacin (FIG. 2E and FIG. 2J) do not change the gross appearance of either PTFE or silk suture. Subtle surface differences are apparent on the titanium screws for Doxycycline Hyclate (FIG. 2M), Erythromycin (FIG. 2L), and Chloramphenicol (FIG. 2N). Levofloxacin coated titanium screws (FIG. 2O) exhibited a white coating with a perceptible change in the surface structure. Presence of antibiotics on implants surfaces can be easily seen by naked eye or under a microscope as a thin film since antibiotics show either a weak color change or a noticeable surface morphology change. However, FTIR spectra before and after antibiotic coating can clearly show the chemical signatures of the antibiotics on the surfaces. FIG. 3 shows the FTIR spectra of the pristine PTFE and doxycycline coated PTFE. Peaks at 1500 and 3000 wavenumber regions are due the doxycycline on PTFE surface. Thickness of the antibiotics on the PTFE and silk suture implant surfaces is an important property which determines the antibiotic dose and effectiveness. The mass of each uncoated and coated sample pieces were measured, and the mass of antibiotic was determined as difference. Average Doxycycline and Erythromycin contents in PTFE by weight were determined as 2.7% and 9.5%, respectively. Note, ellipsometry thickness measurements on glass slide surfaces showed that under identical coating conditions Erythromycin forms much thicker film (aver. 2.3 µm) than Doxycycline (aver. 0.5 µm). Film thicknesses were in good agreement with mass measurements.

Figure 9B:
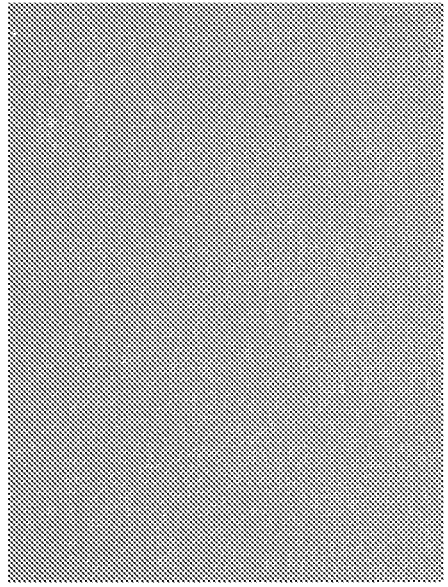
FIGS. 9A-D are microscope images demonstrating that Doxycycline-coated PTFE retains microstructure. PTFE sections were dip-coated in 80 mM Doxycycline Hyclate in 100% ethanol (FIG. 9C and FIG. 9D) or vehicle alone (FIG. 9A and FIG. 9B). Small (5 mm×5 mm) pieces were then cut and imaged a Keyence microscope. Doxycycline coating changes the color but does not alter the microstructure of the PTFE (FIG. 9B and FIG. 9D), which is important for tissue integration.
Figure 9D:
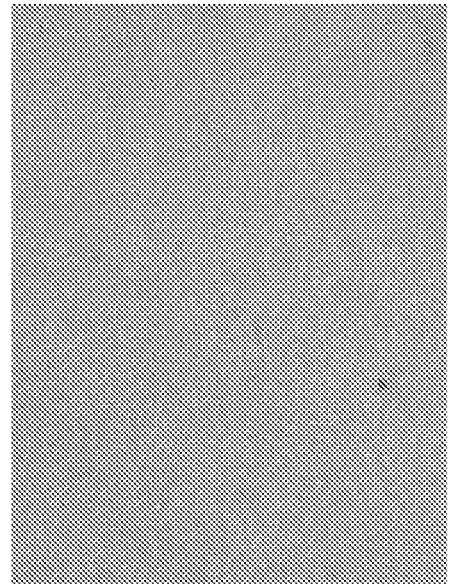
Figure 9A:
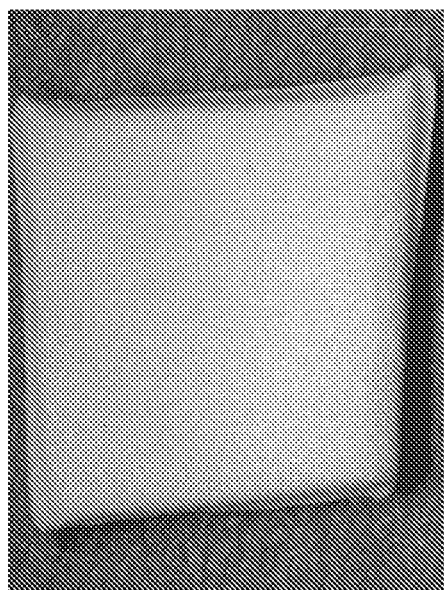
Figure 9C:
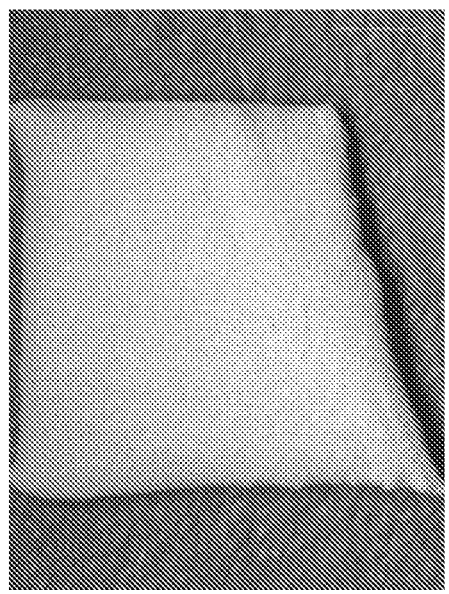
Figure 10B:
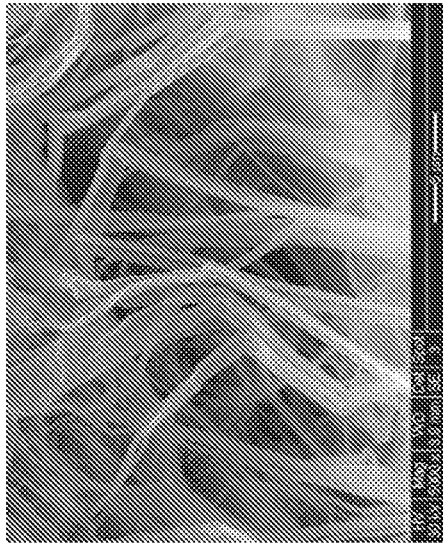
FIGS. 10A-D are scanning electron microscopy images demonstrating that Doxycycline-coated PTFE retains microstructure. PTFE sections were dip-coated in 80 mM Doxycycline Hyclate in 100% ethanol (FIG. 10C and FIG. 10D) or vehicle alone (FIG. 10A and FIG. 10B). Small (5 mm×5 mm) pieces were then cut and imaged with scanning electron microscopy. Doxycycline coating does not obstruct the fine microstructure of the PTFE as seen in the 5000× images (FIG. 10B and FIG. 10D) which is important for tissue integration.
Figure 10D:
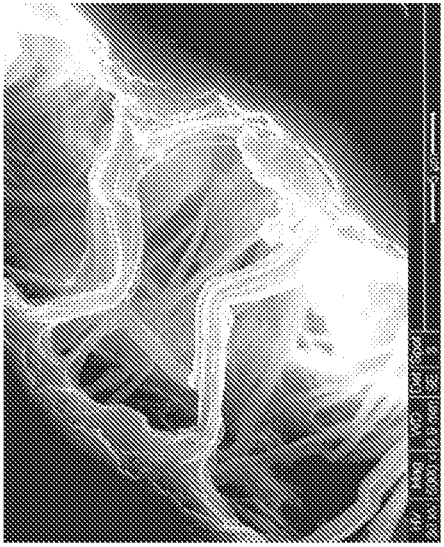
Figure 10A:
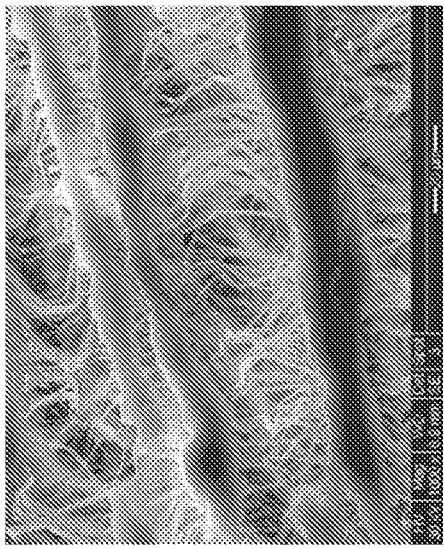
Figure 10C:

Further, Doxycycline coating changes the color but does not alter the microstructure of the PTFE (FIG. 9B, FIG. 9D, FIG. 10B, and FIG. 10D), which is important for tissue integration. FIGS. 9A-D are Keyence microscope images demonstrating that Doxycycline-coated PTFE retains microstructure. PTFE sections were dip-coated in 80 mM Doxycycline Hyclate in 100% ethanol (FIG. 9C and FIG. 9D) or vehicle alone (FIG. 9A and FIG. 9B). FIGS. 10A-D are scanning electron microscopy images demonstrating that Doxycycline-Coated PTFE retains microstructure. PTFE sections were dip-coated in 80 mM Doxycycline Hyclate in 100% ethanol (FIG. 10C and FIG. 10D) or vehicle alone (FIG. 10A and FIG. 10B).

Figure 11B:
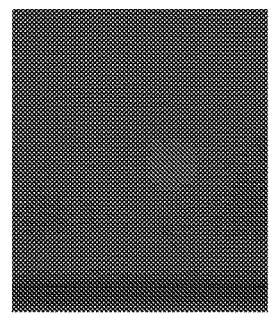
FIGS. 11A-K are pictures demonstrating molecular crystal characterization of various coatings of the instant disclosure. Glass slides were dip-coated in various supersaturated solutions and withdrawn at a rate of 200 mm/s.
Figure 11A:
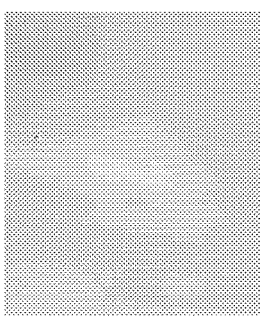
Figure 11E:
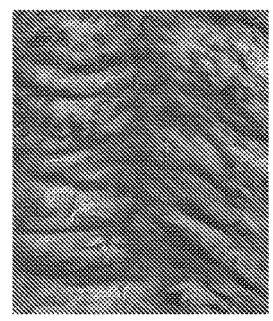
Figure 11D:
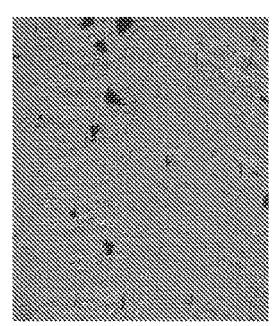
Figure 11C:
Figure 11H:
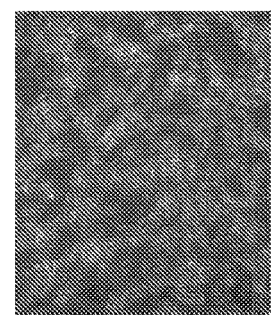
Figure 11G:
Figure 11F:
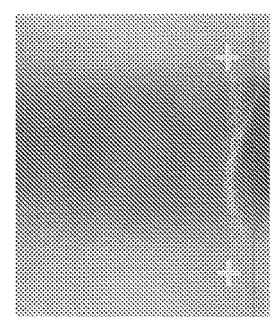
Figure 11K:
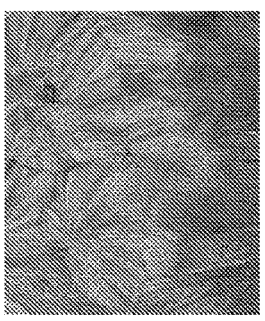
Figure 11J:
Figure 11I:
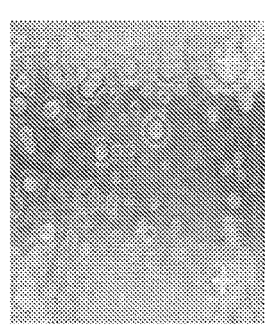

FIGS. 11A-K are pictures further demonstrating molecular crystal characterization of various coatings of the instant disclosure. Glass slides were dip-coated in various supersaturated solutions and withdrawn at a rate of 200 mm/s. FIGS. 11C, F, and I are images were obtained with an iphone; FIGS. 11 A, D, G, and J were obtained using a transmission light microscope at 10× magnification; and FIGS. 11B, E, H, and K were obtained with a polarized light filter. FIGS. 11A-B are 100% ethanol (vehicle), FIGS. 11C-E are 1.9M palmitic acid (in 100% ethanol), FIGS. 11F-G are 1.6M stearlyamine (in 100% ethanol), and FIGS. 11I-K are 2.2M acetylsalicylic acid (in 100% ethanol).

Example 2.3

Antibiotic Coating Prevents MRSA, and *P. aeruginosa* Colonization In Vitro

Antibiotic-coated and vehicle-coated silk suture, PTFE, and titanium screws were immersed in 300 µL bacterial suspension and incubated for 24 hours as described in Example 1.4. As shown in FIGS. 4A-F, Erythromycin, Doxycycline, Chloramphenicol, and Levofloxacin coating significantly reduced MRSA adherent to silk suture in vitro by 5.2 log each (FIG. 4A), adherent to PTFE in vitro by 4.5, 5.7, 5.7, and 3.9 log (FIG. 4B), respectively, and adherent to titanium screws in vitro by 5.3 log each (FIG. 4C) compared to vehicle (100% ethanol)-coated controls (n=15 per group, p<0.05). While Erythromycin, Doxycycline, Chloramphenicol, and Levofloxacin significantly reduced *P. aeruginosa* adherent to silk suture in vitro by 1.6, 4.4, 5.7, and 6.0 log (FIG. 4D), respectively, adherent to PTFE in vitro by 5.8, 5.5, 6.2, and 6.2 log (FIG. 4E), respectively, and adherent to titanium screws in vitro by 5.1, 6.4, 4.5, and 6.4 log (FIG. 4F), respectively, compared to vehicle-coated controls (n=15 per group, p<0.05).

Example 2.4

Antibiotic Coating Reduces MRSA, and *P. aeruginosa* Implant and Local Tissue Colonization In Vivo Antibiotic-coated and vehicle-coated silk sutures, PTFE, and titanium screws were placed subcutaneously and subjected to contamination as described in Example 1.5. Mice were observed and sacrificed after 3 days. Implants were harvested along with tissue from the implant capsule. As shown in FIGS. 5A-F, Erythromycin, Doxycycline, Chloramphenicol, and Levofloxacin coating reduced MRSA colonization of silk suture in vivo by 5.1, 2.1, 1.1, and 4.0 log (FIG. 5A), respectively, colonization of PTFE in vivo by 3.2, 4.7, 2.3, and 3.7 log (FIG. 5B), respectively, and colonization of titanium screws in vivo by 2.5, 3.0, 2.3, and 3.0 log (FIG. 5C), respectively (n=9 per group). Erythromycin, Doxycycline, Chloramphenicol, and Levofloxacin coating reduced *P. aeruginosa* colonization of silk suture in vivo by 0.4, 1.1, 1.9, and 4.3 log (FIG. 5D), respectively, colonization of PTFE in vivo by 3.3, 2.7, 2.8, and 3.7 log (FIG. 5E), respectively, and colonization of titanium screws in vivo by 0.4, 2.8, 2.5, and 3.3 log (FIG. 5F), respectively (n=9 per group).

Example 2.5

Antibiotic Coatings Decreases Local Tissue Inflammation

Figure 6B:
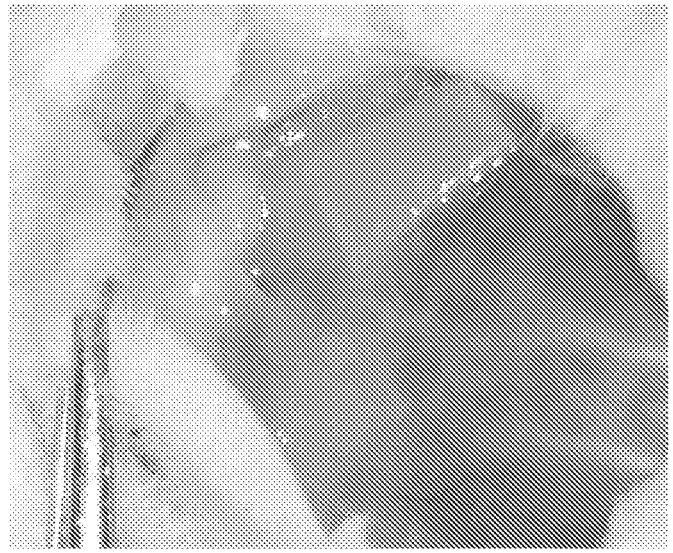
FIGS. 6A-B are images demonstrating that Doxycycline coated implants prevent local inflammation after implant infection. Male CF-1 mice underwent subcutaneous PTFE implantation with either ethanol coated (FIG. 6A) or Doxycycline coated (FIG. 6B) implants followed by contamination with 2.5 million cfu S. aureus in 100 µL 0.9% NaCl. Mice were sacrificed after 7 days and tissue was evaluated prior to implant and tissue harvest.
Figure 6A:
Figure 7B:
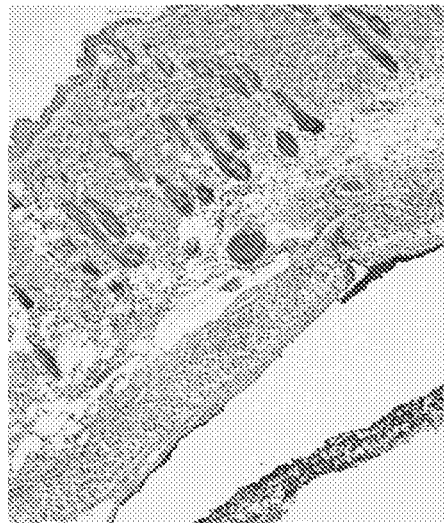
FIGS. 7A-D are Hematoxylin and Eosin staining images demonstrating that Doxycycline-coated implants prevent local inflammation after implant infection. Male CF-1 mice underwent subcutaneous PTFE implantation with either ethanol coated (FIG. 7A and FIG. 7C) or Doxycycline-coated (FIG. 7B and FIG. 7D) implants followed by contamination with 2.5 million cfu S. aureus in 100 µL 0.9% NaCl (FIG. 7C and FIG. 7D) or 100 µL sterile 0.9% NaCl (FIG. 7A and FIG. 7B). Skin, implant capsule, and subcutaneous tissue were harvested en bloc after 7 days, fixed, and processed. Hematoxylin and Eosin staining were performed on tissue sections.
Figure 7D:
Figure 7A:
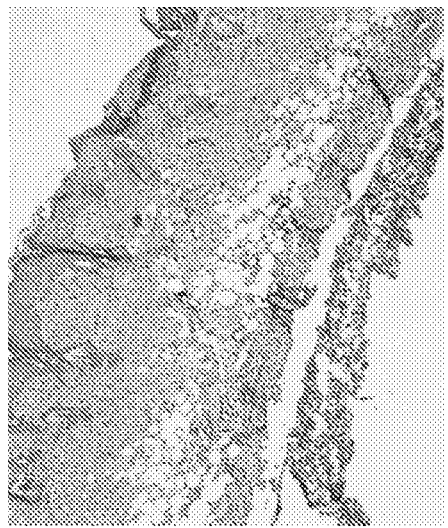
Figure 7C:
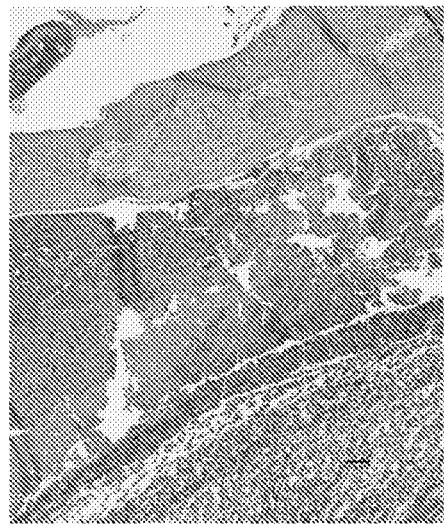
Figure 8B:
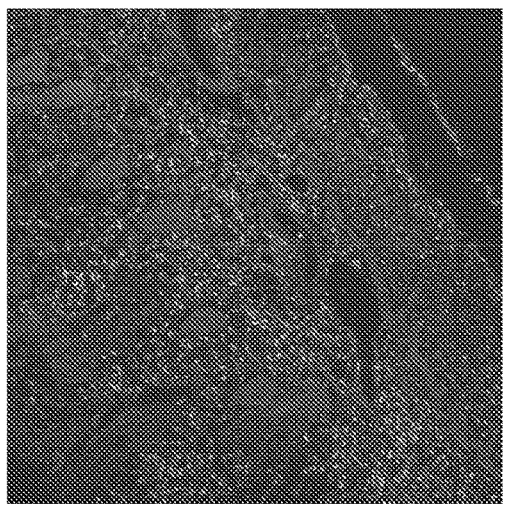
FIGS. 8A-D are confocal fluorescent microscopy images that demonstrate Doxycycline-coated implants prevent local inflammation after implant infection. Male CF-1 mice underwent subcutaneous PTFE implantation with either ethanol coated (FIG. 8A and FIG. 8C) or Doxycycline-coated (FIG. 8B and FIG. 8D) implants followed by contamination with 2.5 million cfu S. aureus in 100 µL 0.9% NaCl (FIG. 8C and FIG. 8D) or 100 µL sterile 0.9% NaCl (FIG. 8A and FIG. 8B). Skin, implant capsule, and subcutaneous tissue was harvested en bloc after 7 days, fixed, and processed. Immunohistochemistry was performed on tissue sections for Ly6-g, a neutrophil marker.
Figure 8D:
Figure 8A:
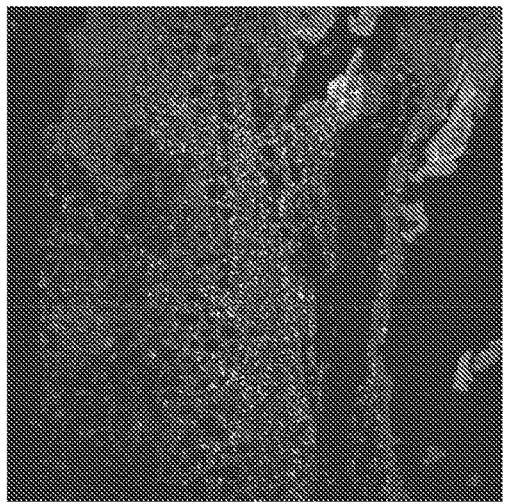
Figure 8C:
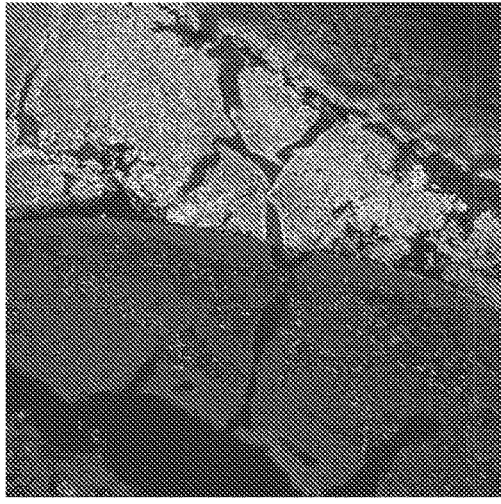

Doxycycline-coated implants and vehicle-coated implants were placed subcutaneously in mice and the mice were infected with MRSA as described in Example 1.5. Additionally, Doxycycline-coated and vehicle-coated implants were placed in mice without infection for comparative analysis. After 3 days, the skin, implant, and implant capsule were harvested en bloc, fixed, and stained. Abcess formation and local inflammation are prevented around Doxycycline-coated implants after infection with 2.5 million cfu MRSA (FIG. 6B). FIGS. 7A-D and FIGS. 8A-D show an absence of inflammation as evidenced by the paucity of leukocytes in FIG. 7A, FIG. 7B, and FIG. 7D, as well as positive Ly6-C/G cells in FIG. 8A, FIG. 8B, and FIG. 8D around both doxycycline and vehicle coated implants when no infection was initiated, and around Doxycycline-coated implants when infection was initiated, respectively. Abscess formation occurs around vehicle coated implants after infection with 2.5 million cfu MRSA as evidenced by the gross appearance of tissues in FIG. 6A, leukocyte accumulation in FIG. 7C, and positive Ly6-C/G staining in FIG. 8C.

Example 2.6

Figure 12A:
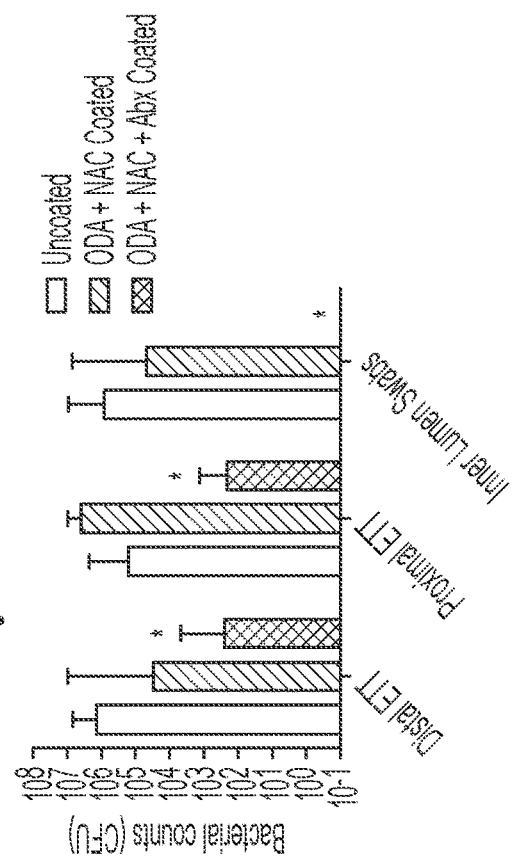
FIGS. 12A-C are graphs demonstrating that antimicrobial coatings reduce bacterial loads on endotracheal tubes and in lungs. Adult female pigs were anesthetized and intubated with either uncoated, Octadecylamine (ODA)/N-acetyl cysteine (NAC) coated, or ODA/NAC/doxycycline+levofloxacin (Abx) coated tubes and mechanically ventilated under sedation for up to 72 hours. Portions of the lungs (right upper lobe (RUL), right lower lobe (RLL), left upper lobe (LUL), and left lower lobe (LLL)) and trachea were harvested after the pigs either died, or were sacrificed at the study endpoint (72 hours). Lungs were homogenized and bacteria quantified in the homogenate by the plate dilution method. Trachea and endotracheal tube pieces were placed in neutralizing broth and immersed in a sonicating bath for 10 min to release adherent bacteria. Bacteria were quantified with the plate dilution method.
Figure 12B:
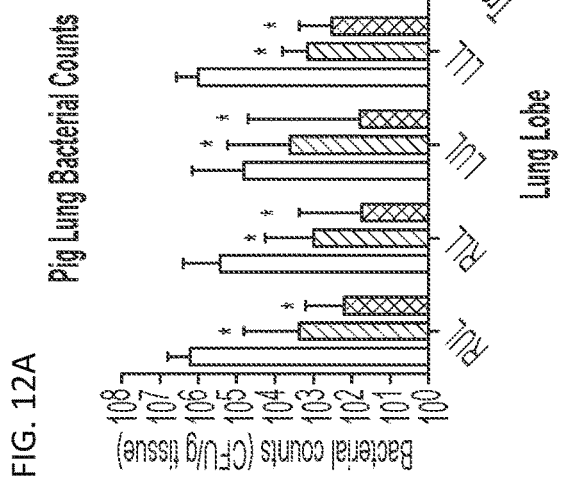
Figure 12C:
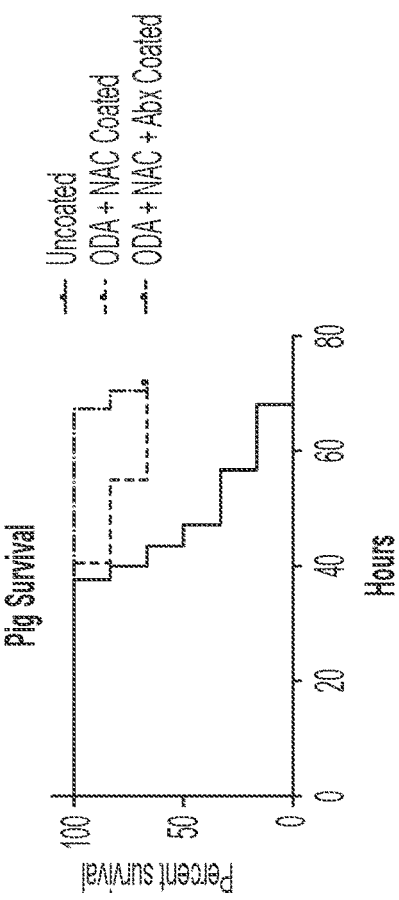

Antimicrobial Coatings Reduce Bacterial Loads on Endotracheal Tubes and in Lungs Adult female pigs were anesthetized and incubated with either uncoated, Octadecylamine (ODA)/N-acetyl cysteine (NAC) coated, or ODA/NAC/doxycycline+levofloxacin (Abx) coated tubes and mechanically ventilated under sedation for up to 72 hours as described in Example 1.9. Portions of the lungs (right upper lobe (RUL), right lower lobe (RLL), left upper lobe (LUL), and left lower lobe (LLL)) and trachea were harvested after the pigs either died, or were sacrificed at the study endpoint (72 hours). Lungs were homogenized and bacteria quantified in the homogenate by the plate dilution method. Trachea and endotracheal tube pieces were placed in neutralizing broth and immersed in a sonicating bath for 10 min to release adherent bacteria. Bacteria were quantified with the plate dilution method. FIG. 12A demonstrates that ODA/NAC and ODA/NAC/Abx coated tubes significantly reduced the amount of bacteria (>2 log) in the lungs of intubated pigs. FIG. 12B demonstrates that ODA/NAC/Abx coating significantly reduced the amount of adherent bacteria (>2 log) to the surface of endotracheal tubes. FIG. 12C shows that ODA/NAC and ODA/NAC/Abx significatly improved survival times of intubated pigs.

Although embodiments of the invention have been exemplified and described with specificity, a person of ordinary skill in the art will understand that additional aspects and embodiments are within the scope of the claims as defined by the appended claims.

The invention claimed is:

1. A method for applying an antibiotic coating to a surface of a substrate, the method comprising:
 a) admixing at least one antibiotic in a fast-evaporating or medium-evaporating organic solvent and applying energy to the admixture to provide a saturated or supersaturated solution, wherein applying energy comprises bath or probe sonicating at an ultrasonic frequency; and
 b) coating the surface of the substrate with at least one application of the solution, each application followed directly by a solvent evaporation period.

2. The method according to claim 1, wherein step b) further comprises bringing the coated substrate to ambient temperature such that the solvent evaporation period takes place at room temperature.

3. The method according to claim 1, wherein the antibiotic is selected from one or more of doxycycline, chloramphenicol, erythromycin, and levofloxacin.

4. The method according to claim 1, wherein the organic solvent of step (a) is a fast-evaporating organic solvent and exhibits a vaporization rate under ambient conditions of greater than 3 based on an n-butyl acetate standard=1.

5. The method according to claim 4, wherein the solvent is selected from hexane, acetone, cyclohexane, and methyl ethyl ketone.

6. The method according to claim 1, wherein the organic solvent of step (a) is a medium-evaporating organic solvent and exhibits a vaporization rate under ambient conditions of between 0.8 and 3.0, inclusive, based on an n-butyl acetate standard=1.

7. The method according to claim 6, wherein the solvent is selected from ethanol and naphtha.

8. The method according to claim 6, wherein the solvent is 95% to 100% ethanol.

9. The method according to claim 1, wherein the coating of step (b) comprises dip-coating, spray-coating, or spin-coating.

10. The method according to claim 1, wherein step (b) comprises at least 2 applications of coating.

11. The method according to claim 1, wherein the substrate is selected from glass, plastic, polymer, or metal.

12. The method according to claim 1, wherein applying energy further comprises heating to a temperature less than the solvent boiling point.

13. The method according to claim 12, comprising heating to within 10° C. of the solvent boiling point.

14. The method according to claim 12, comprising heating to within 10° C. of the solvent boiling point and sonicating at about 40 kHz.

15. The method according to claim 1, wherein the solvent evaporation period is at least partially effectuated by one or more of air drying, blow-drying, vacuum-drying or heat-assisted drying.

16. The method of claim 1, wherein the solvent evaporation period is sufficient for evaporation of the solvent to form a stable liquid crystalline mesophase material of the at least one antibiotic in solvent.

17. The method of claim 1, wherein the solvent evaporation period is sufficient for evaporation of the solvent to form a reverse stable liquid crystalline mesophase material of solvent in the at least one antibiotic.

18. The method of claim 1, wherein the solvent evaporation period is sufficient for substantially complete evaporation of solvent to form an antibiotic molecular crystal film coating.

19. The method according to claim 1, wherein the antibiotic is selected from one or more of doxycycline, chloramphenicol, erythromycin, and levofloxacin and the solvent is ethanol.

* * * * *

UNITED STATES PATENT AND TRADEMARK OFFICE
CERTIFICATE OF CORRECTION

PATENT NO. : 11,517,650 B2
APPLICATION NO. : 16/758508
DATED : December 6, 2022
INVENTOR(S) : Aaron Seitz et al.

Page 1 of 1

It is certified that error appears in the above-identified patent and that said Letters Patent is hereby corrected as shown below:

In the Specification

In Column 1, Line(s) 50, after "with", delete --with--.

In Column 1, Line(s) 65, after "an", delete --an--.

In Column 3, Line(s) 66, delete "2A-0", insert --2A-O--, therefor.

In Column 5, Line(s) 56, delete "microsope", insert --microscope--, therefor.

In Column 6, Line(s) 17, delete "sigificatly", insert --significantly--, therefor.

In Column 17, Line(s) 38, delete "microsope", insert --microscope--, therefor.

In Column 19, Line(s) 12, delete "sigificatly", insert --significantly--, therefor.

Signed and Sealed this
Twenty-sixth Day of March, 2024

Katherine Kelly Vidal
*Director of the United States Patent and Trademark Office*